United States Patent [19]

Suhac et al.

[11] 4,354,940

[45] Oct. 19, 1982

[54] SODIUM ALUMOGLUCOHEPTONATE, A PROCESS FOR ITS PREPARATION AND ITS USE AS SEQUESTERING AGENT

[75] Inventors: Peter Suhac; Natasa Hafner-Milac; Bozidar Dolenc, all of Ljubljana, Yugoslavia

[73] Assignee: LEK, tovarna farmacevtskih in kemicnih izdelkov, n.sol.o., Ljubljana, Yugoslavia

[21] Appl. No.: 281,744

[22] Filed: Jul. 9, 1981

[30] Foreign Application Priority Data

Feb. 14, 1979 [YU] Yugoslavia .......................... 354/79

[51] Int. Cl.³ .................................................. C02F 5/10
[52] U.S. Cl. ........................................ 210/698; 134/2; 252/156; 252/174.18; 252/DIG. 11
[58] Field of Search .................... 134/2; 252/156, 180, 252/181, 174.17, 174.18, DIG. 11; 260/448 B, 429 J; 210/698

[56] References Cited

U.S. PATENT DOCUMENTS

| 1,846,880 | 2/1932 | Kussmaul | 260/448 R |
| 2,327,815 | 8/1943 | Niedercorn et al. | 260/448 R |
| 3,014,055 | 12/1961 | Johnson | 260/448 R |
| 3,200,136 | 8/1965 | Grossmith | 260/448 B |
| 3,391,176 | 7/1968 | Grossmith | 260/429 J |
| 3,539,463 | 11/1970 | Harper et al. | 252/181 |
| 3,539,464 | 11/1970 | Harper et al. | 252/181 |
| 3,553,316 | 1/1971 | Rubino | 260/429 J |

FOREIGN PATENT DOCUMENTS

1112773 5/1968 United Kingdom .

*Primary Examiner*—Benoit Castel
*Attorney, Agent, or Firm*—Pollock, Vande Sande & Priddy

[57] ABSTRACT

Sodium alumoglucoheptonate, process of preparing from sodium glucoheptonate and sodium aluminate, and use of sodium alumoglucoheptonate as a sequestering agent.

18 Claims, No Drawings

SODIUM ALUMOGLUCOHEPTONATE, A PROCESS FOR ITS PREPARATION AND ITS USE AS SEQUESTERING AGENT

This is a division of application Ser. No. 118,952, filed Feb. 6, 1980, now U.S. Pat. No. 4,297,293.

This invention relates to sodium alumoglucoheptonate, to a process for its preparation and to its use as sequestering agent.

It is known that sodium cyanide react with glucose in aqueous solution, yielding two epimeric sodium glucoheptonates. There are formed approximately 70% of the epimer which crystallizes as dihydrate, i.e. sodium D-glycero-D-guloheptonate, and 30% of the epimer which does not crystallize, i.e. sodium D-glycero-D-ido-heptonate. From the reaction mixture a substantial part of sodium D-glycero-D-guloheptonate can be recovered by crystallization and isolated by filtration. In addition to the crystalline sodium glucoheptonate, there is obtained a more or less concentrated solution of sodium glucoheptonate of a yellow to reddish brown colour. This solution usually contains 35% of solids, which are substantially sodium D-glycero-D-ido-heptonate, but is still contains a certain amount of sodium D-glycero-D-gulo-heptonate. Crystalline sodium glucoheptonate, i.e. sodium D-glycero-D-gulo-heptonate, and the solution of sodium glucoheptonate, which is mainly sodium D-glycero-D-ido-heptonate, are commercial articles and are used as sequestering agents, especially for calcium and iron in aqueous sodium hydroxide solutions. The sequestering properties of the solution, however, are not quite so good as those of crystalline sodium glucoheptonate. Another disadvantage of the solution is its high water content and hence the solution is not suitable for transportation over longer distances. In some specific cases the use of a liquid sequestering agent is not desirable at all. As already mentioned, sodium D-glycero-D-ido-heptonate, which is the main constituent of the sodium glucoheptonate solution, does not crystallize. From the sodium glucoheptonate solution, which is obtained in the production of crystalline sodium glucoheptonate, it is practically impossible to obtain a dry free-flowing product, which is preferred by the customers to the liquid form. Evaporation or drying of the solution produces an amorphous hygroscopic and sticky glassy mass, which melts already at about 60° C. Therefore this solution cannot bespray-dried as the particles adhere to the walls of the drier and to each other. Owing to these properties, the solution of sodium glucoheptonate represents an unwanted by-product at the production of crystalline sodium glucoheptonate.

It is known that in the solution of sodium glucoheptonate, in which an appropriate amount of boric acid or sodium metaborate or tetraborate has been used, there are formed chelate compounds which are known as sodium boroglucoheptonate, whenever the solution contains either of the two epimeric sodium glucoheptonates or any mixture of both epimers. In contrast with the starting solution, the solution of sodium boroglucoheptonate, which is usually prepared from a solution of sodium glucoheptonate representing a by-product of the preparation of crystalline sodium glucoheptonate, can be spray-dried readily and without problems. The obtained sodium boroglucoheptonate is a free-flowing powder and can be used similarly to the sodium glucoheptonate as sequestering agent.

It has now been found that sodium aluminate reacts with sodium glucoheptonate too. When sodium aluminate solution is added to the solution of sodium glucoheptonate representing a by-product of the preparation of crystalline sodium glucoheptonate, there is formed a solution of sodium alumoglucoheptonate, which can be spray-dried readily and without problems. The obtained sodium alumoglucoheptonate is a free-flowing nonhygroscopic powder.

The first object of the invention is sodium alumoglucoheptonate of the general formula

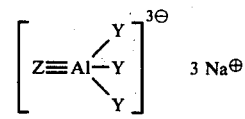

wherein

Z represents a residue of the formula

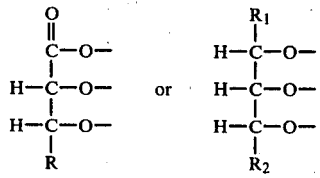

wherein
- R represents a residue of a molecule of sodium D-glycero-D-gulo-heptonate or of sodium D-glycero-D-ido-heptonate and
- $R_1$ and $R_2$ represent moieties of a molecule of sodium D-glycero-D-gulo-heptonate or of sodium D-glycero-D-ido-heptonate,
- Y represents a hydroxy group or three Y are joined to represent the residue Z.

The second object of the invention is a process for the preparation of sodium alumoglucoheptonate, which is characterized in that a solution of sodium aluminate solution is added to a solution of sodium glucoheptonate in such a quantity that the ratio between the number of aluminum atoms and the number of sodium glucoheptonate molecules amounts to from 0.50:1 to 1.50:1 and the resulting solution is optionally spray-dried at an inlet air temperature of 180° to 200° C. and outlet air temperature of 90° to 100° C. to recover sodium alumoglucoheptonate in powder form.

The third object of the invention is the use of sodium alumoglucoheptonate as sequestering agent for calcium and ferric ions.

It is believed that in an aqueous solution of sodium alumoglucoheptonate there exists an equilibrium between the following complexes.

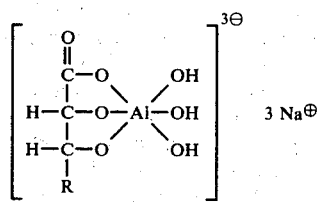

I

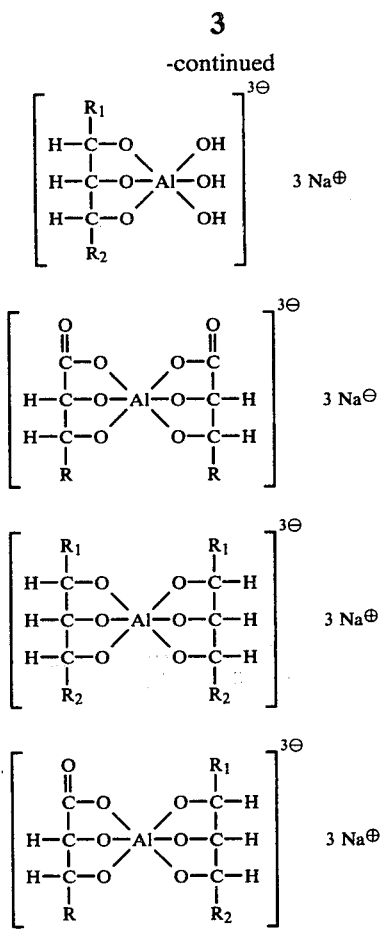

In the formulae I to V

R represents a residue of a molecule of sodium D-glycero-D-gulo-heptonate or of sodium D-glycero-D-ido-heptonate, and $R_1$ and $R_2$ represent moieties of a molecule of sodium D-glycero-D-gulo-heptonate or of sodium D-glycero-D-ido-heptonate.

The present invention, however, is completely independent of a possible later confirmation or rejection of the above theory about the chemical nature of sodium alumoglucoheptonate.

The sodium aluminate solution is obtained by dissolving sodium aluminate in water. Sodium aluminate is a commercial article and is less expensive than borax, considering the fact that the latter contains about 47% of water of crystallization. Sodium aluminate (technical grade) normally contains 54% of $Al_2O_3$ and 41% of $Na_2O$, the mole ratio of $Na_2O/Al_2O_3$ being 1.25:1.

The sodium aluminate solution can also be obtained by dissolving hydrated alumina in hot concentrated sodium hydroxide solution. Hydrated alumina is an intermediate in the production of alumina and aluminum and is produced in enormous quantities, being therefore exceptionally low priced. Sodium hydroxide is also a basic chemical and is low priced. By the use of hydrated alumina and of sodium hydroxide instead of sodium aluminate, the costs of production of sodium aluminoglucoheptonate can be substantially reduced. In case of the preparation of sodium aluminate from hydrated alumina and aqueous solution of sodium hydroxide, an excess of sodium hydroxide is necessary to ensure a $Na_2O/Al_2O_3$ ratio of 1.2 to 1.3:1. Because of the excess of sodium hydroxide, sodium alumoglucoheptonate shows in its aqueous solution an alkaline reaction. The pH of a 10% solution is 11.5.

Furthermore it has been found that in sodium hydroxide solutions sodium alumoglucoheptonate, obtained in the abovedescribed manner, has a capacity for sequestering calcium ions which is even superior to the sequestering capacity of known sequestering agents which are used in alkaline solutions. The sequestering capacity of sodium alumoglucoheptonate for calcium ions depends on its composition, i.e. on the molar ratio of the used reactants. It has been found that the sequestering capacity of sodium alumoglucoheptonate is at its greatest when it contains 1 molecule of sodium aluminate (NaAlO$_2$), i.e. 1 atom of aluminum per 1 molecule of sodium glucoheptonate.

From the solution of sodium glucoheptonate, which consists of a mixture of sodium D-glycero-D-ido-heptonate and D-glycero-D-gulo-heptonate and which represents a by-product at the preparation of crystalline sodium glucoheptonate, samples of sodium alumoglucoheptonate containing 0.50, 0.75, 1.00, 1.25 and 1.50 atoms resp. of aluminum per molecule of sodium glucoheptonate and a sample of sodium boroglucoheptonate containing 1 atom of boron per molecule of sodium glucoheptonate were prepared. Sequestering capacity of the solutions of sodium glucoheptonate, representing a by-product at the preparation of crystalline sodium glucoheptonate, and of samples of sodium alumoglucoheptonate and of sodium boroglucoheptonate prepared thereof, as well as of crystalline sodium glucoheptonate and sodium gluconate for calcium ions were determined. The results are shown in Table I and refer to 24 hr. stability [cf. C. L. Mehltretler et al., Sequestration by Sugar Acids, Ind. Eng. Chem. 45, 2782-4(1953)].

TABLE I

| Sequestering agents | Sequestering capacity, expressed in g of calcium, sequestered by 100 g of anhydrous sequestering agent at room temperature in a solution containing | | |
|---|---|---|---|
| | 1% NaOH | 3% NaOH | 5% NaOH |
| Sodium gluconate | 0.4 | 2.4 | 7.1 |
| Sodium glucoheptonate, crystalline | 0.2 | 2.7 | 8.1 |
| Sodium glucoheptonate, solution | 0.2 | 0.7 | 6.4 |
| Sodium boroglucoheptonate, (1:1)[x] | 1.5 | 2.6 | 4.6 |
| Sodium alumoglucoheptonate (0.50:1)[xx] | 8.7 | 9.6 | 9.6 |
| Sodium alumoglucoheptonate (0.75:1)[xx] | 10.7 | 12.0 | 9.9 |
| Sodium alumoglucoheptonate (1.00:1)[xx] | 11.2 | 12.2 | 12.2 |
| Sodium alumoglucoheptonate (1.25:1)[xx] | 11.4 | 11.4 | 11.4 |
| Sodium alumoglucoheptonate (1.50:1)[xx] | 11.2 | 10.6 | 10.3 |

[x]ratio between the number of atoms of boron and the number of molecules of sodium glucoheptonate
[xx]ratio between the number of atoms of aluminum and the number of molecules of sodium glucoheptonate The sequestering capacity of the same samples for ferric ions were determined according to a modified method of the above-cited author. The results are shown in Table II.

TABLE II

| Sequestering agents | Sequestering capacity, expressed in g of iron, sequestered by 100 g of anhydrous sequestering agent at room temperature in a solution containing | | |
|---|---|---|---|
| | 1% NaOH | 3% NaOH | 5% NaOH |
| Sodium gluconate | 330 | 330 | 299 |
| Sodium glucoheptonate, crystalline | 359 | 377 | 307 |
| Sodium glucoheptonate, solution | 296 | 248 | 216 |
| Sodium boroglucoheptonate, (1:1)* | 288 | 222 | 189 |
| Sodium alumoglucoheptonate (0.50:1)** | 254 | 189 | 172 |
| Sodium alumoglucoheptonate (0.75:1)** | 261 | 193 | 143 |
| Sodium alumoglucoheptonate (1.00:1)** | 249 | 163 | 129 |
| Sodium alumoglucoheptonate (1.25:1)** | 219 | 149 | 96 |
| Sodium alumoglucoheptonate (1.50:1)** | 178 | 120 | 70 |

*ratio between the number of atoms of boron and the number of molecules of sodium glucoheptonate
**ratio between the number of atoms of aluminum and the number of molecules of sodium glucoheptonate From the above results it can be seen that in 1 to 5% sodium hydroxide solutions sodium alumoglucoheptonate as a sequestering agent for calcium is several times more effective than sodium boroglucoheptonate, glucoheptonate and gluconate. At the same time sodium alumoglucoheptonate is a good sequestering agent for iron.

A typical example of the use of such sequestering agents is the washing of bottles with a 1 to 3% solution of sodium hydroxide in breweries and soft drinks production. Ordinary tap water is used for preparing the sodium hydroxide solution and in washing. Because of the alkalinity, calcium and magnesium salts which are present in tap water separate therefrom to form precipitates, which deposit on both the wash machinery and the bottles being washed, causing stains of scale (milkstone). On the bottles to be washed, there are also rust stains, originating from contact with iron, especially on the neck of the bottle from contact with crown cork closures that are commonly made of sheet iron. The scale formation is prevented and rust stains are removed by adding a sequestering agent to the sodium hydroxide solution. The sequestering agent used should possess as high a sequestering capacity as possible for both calcium and iron.

It has also been found that sodium alumoglucoheptonate, prepared from the complete reaction mixture, i.e. without previous isolation of crystalline sodium glucoheptonate, shows practically the same sequestering properties.

The following Examples illustrate the invention without limiting its scope.

EXAMPLE 1

A solution of hydrogen peroxide (35%, 93 ml) was added to a solution of sodium glucoheptonate (28.8%, 11.6 kg), which had remainded after the separation of the major part of crystalline sodium glucoheptonate and was of a yellow to reddish brown colour and from which practically all ammonia, which had been formed in the reaction between the glucose and sodium cyanide, was removed. After some time the solution of sodium glucoheptonate became lighter in colour. A solution of sodium aluminate, obtained by boiling hydrated alumina (1089 g), containing 63.2% of $Al_2O_3$, in a solution of sodium hydroxide (702 g) and demineralized water (500 ml) was added. The obtained solution of sodium alumoglucoheptonate was filtered and spray-dried at an air inlet temperature of about 180° to 200° C. and an air outlet temperature of about 90° to 100° C. There were obtained 4737 g of the product with a moisture content of 5.15% in the form of a free-flowing powder.

EXAMPLE 2

The procedure of Example 1 was repeated. In this instance, however, a solution of sodium aluminate, obtained by boiling hydrated alumina (544.5 g), containing 63.2% of $Al_2O_3$, in a solution of sodium hydroxide (351 g) and demineralized water (250 ml), was added to the solution (11.6 kg) of sodium glucoheptonate of the Example 1. There were obtained 4183 g of the product with a moisture content of 5.27% in the form of a free-flowing powder.

EXAMPLE 3

The procedure of Example 1 was repeated. In this instance, however, a solution of sodium aluminate, obtained by boiling hydrated alumina (1633.5 g), containing 63.2% of $Al_2O_3$, in a solution of sodium hydroxide (1057 g) and demineralized water (750 ml), was added to the solution (11.6 kg) of sodium glucoheptonate of Example 1. There were obtained 5519 g of a product with a moisture content of 4.98% in the form of a free-flowing powder.

EXAMPLE 4

Sodium cyanide (265 g) was dissolved in demineralized water (3200 ml) and glucose (monohydrate) (1000 g) was added thereto at stirring. The mixture was allowed to stand for 3 to 4 days at room temperature until the reaction was completed and then a hydrogen peroxide solution (50 ml, 35%) was added thereto. In this way the excess of cyanide was destroyed and the reaction mixture became lighter in colour. Ammonia was removed by bubbling air through the reaction mixture or by means of vacuum.

A solution of sodium aluminate, obtained by boiling hydrated alumina (405 g), containing 63.2% of $Al_2O_3$, in a solution of sodium hydroxide (261 g) and demineralized water (186 ml), was added thereto. The obtained solution of sodium alumoglucoheptonate was filtered and dried in the same way as in Example 1. There were obtained 1795 g of the product with a moisture content of 5.13 g in the form of a free-flowing powder.

EXAMPLE 5

The procedure of Example 4 was repeated. In this instance, however, a solution of sodium aluminate, obtained by boiling hydrated alumina (202.5 g), containing 63.2% of $Al_2O_3$, in a solution of sodium hydroxide (130.5 g) and demineralized water (93 ml), was added to the reaction mixture, obtained from sodium cyanide (265 g) and glucose (1000 g). There were obtained 1584 g of a product with a moisture content of 5.21% in the form of a free-flowing powder.

EXAMPLE 6

The procedure of Example 4 was repeated. In this instance, however, a solution of sodium aluminate, obtained by boiling hydrated alumina (607.5 g), containing 63.2% of $Al_2O_3$, in a solution of sodium hydroxide (391.5 g) and demineralized water (279 ml), was added to the reaction mixture, obtained from sodium cyanide (265 g) and glucose (1000 g). There were obtained 2094 g of a product with a moisture content of 5.09% in the form of a free-flowing powder.

What is claimed is:

1. A method for washing bottles, which comprises contacting the bottles with an aqueous solution containing sodium alumoglucoheptonate of the formula:

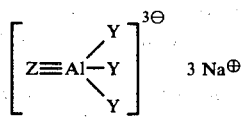

wherein

Z represents a residue of the formula

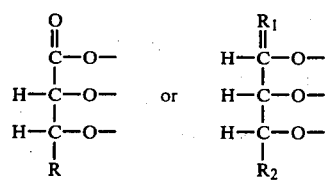

wherein

R represents a residue of a molecule of sodium D-glycero-D-gulo-heptonate or of sodium D-glycero-D-ido-heptonate, and $R_1$ and $R_2$ represent moieties of a molecule of sodium D-glycero-D-gulo-heptonate or of sodium D-glycero-D-ido-heptonate, and Y represents a hydroxy group or three Y are joined to represent the residue Z.

2. A method for washing bottles which comprises contacting the bottles with an aqueous solution containing sodium alumoglucoheptonate obtained by adding a solution of sodium aluminate to a solution of sodium glucoheptonate in such a quantity that the ratio between the number of aluminum atoms and the number of sodium glucoheptonate molecules amounts to from 0.50:1 to 1.50:1.

3. A method for sequestering iron ions or calcium ions which comprises contacting said ions with sodium alumoglucoheptonate of the formula:

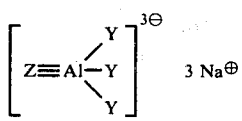

wherein

Z represents a residue of the formula

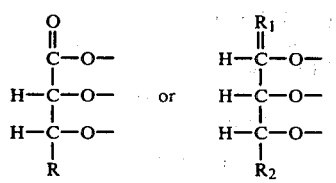

wherein

R represents a residue of a molecule of sodium D-glycero-D-gulo-heptonate or of sodium D-glycero-D-ido-heptonate, and $R_1$ and $R_2$ represent moieties of a molecule of sodium D-glycero-D-gulo-heptonate or of sodium D-glycero-D-ido-heptonate, Y represents a hydroxy group or three Y are joined to represent the residue Z.

4. A method for sequestering iron ions or calcium ions which comprises contacting said ions with sodium alumoglucoheptonate obtained by adding a solution of sodium aluminate to a solution of sodium glucoheptonate in such a quantity that the ratio between the number of aluminum atoms and the number of sodium glucoheptonate molecules amounts to from 0.50:1 to 1.50:1.

5. The method of claim 3 or claim 4 wherein said sodium alumoglucoheptonate is in the form of an aqueous solution.

6. The method of claim 3 or claim 4 wherein said ions include iron ions.

7. The method of claim 3 or claim 4 wherein said ions include calcium ions.

8. The method of claim 1 or claim 2 wherein said solution contains 1 to 5% NaOH.

9. The method of claim 1 or claim 4 wherein Z represents a residue of the formula:

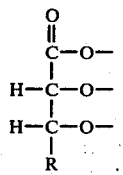

10. The process of claim 9 wherein each Y represents a hydroxy group.

11. The process of claim 9 wherein three Y groups are joined to represent a residue of the formula:

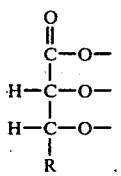

12. The process of claim 9 wherein three Y groups are joined to represent a residue of the formula:

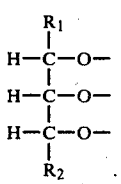

13. The method of claim 1 or claim 4 wherein Z represents a residue of the formula:

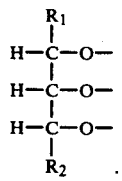

14. The process of claim 13 wherein each Y represents a hydroxy group.

15. The process of claim 13 wherein three Y groups are joined to represent a residue of the formula:

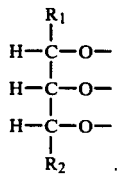

16. The method of claim 1 or claim 4 wherein each Y represents a hydroxy group.

17. The method of claim 1 or claim 4 wherein three Y groups are joined to represent a residue of the formula:

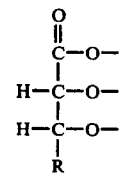

18. The method of claim 1 or claim 4 wherein three Y groups are joined to represent a residue of the formula:

$$\begin{array}{c} R_1 \\ | \\ H-C-O- \\ | \\ H-C-O- \\ | \\ H-C-O- \\ | \\ R_2 \end{array}$$

* * * * *